United States Patent [19]

Friedman et al.

[11] Patent Number: 5,484,709
[45] Date of Patent: Jan. 16, 1996

[54] IMMUNOASSAY METHOD FOR DETECTING AN IMMUNOLOGICALLY NON-REMARKABLE COMPOUND, ITS COMPONENTS AND A KIT FOR USE IN PERFORMING THE SAME

[75] Inventors: Stephen B. Friedman, Chapel Hill; Randy L. Allen, Apex; Thomas N. Stewart, Durham, all of N.C.

[73] Assignee: Ensys, Inc., Research Triangle Park, N.C.

[21] Appl. No.: 118,675

[22] Filed: Sep. 10, 1993

[51] Int. Cl.[6] .......................... G01N 33/577; C07K 16/44
[52] U.S. Cl. .................. 435/7.93; 435/188; 436/533; 436/545; 436/546; 530/388.9; 530/404; 530/405; 530/807
[58] Field of Search .................. 435/7.93, 188; 530/388.9, 404, 405, 807; 436/533, 545, 546

[56] References Cited

U.S. PATENT DOCUMENTS

| | | | |
|---|---|---|---|
| 3,676,076 | 7/1972 | Grady | 422/101 |
| 3,879,262 | 4/1975 | Schuurs et al. | 424/12 |
| 4,022,878 | 5/1977 | Gross | 424/12 |
| 4,208,187 | 6/1980 | Givner | 422/101 |
| 4,249,904 | 2/1981 | Rounbehler et al. | 422/88 |
| 4,393,141 | 7/1983 | Schlueter et al. | 422/101 |
| 4,483,921 | 11/1984 | Cole | 435/810 |
| 4,786,594 | 11/1988 | Khanna et al. | 436/503 |
| 4,952,513 | 8/1990 | Koocher | 436/182 |
| 5,183,740 | 2/1993 | Ligler et al. | 435/7.32 |
| 5,200,153 | 4/1993 | Carr et al. | 422/102 |

FOREIGN PATENT DOCUMENTS

| | | |
|---|---|---|
| 0242589 | 10/1987 | European Pat. Off. . |
| 1-269486 | 10/1989 | Japan . |
| 1-269487 | 10/1989 | Japan . |
| 1-269488 | 10/1989 | Japan . |
| 1-269485 | 10/1989 | Japan . |
| WO88/09798 | 12/1988 | WIPO . |

OTHER PUBLICATIONS

C. Keuchel et al., Vom Wasser, vol. 81, pp. 7–15 (1993).
M. O'Sullivan et al., Annals of Biochem., vol. 16, pp. 221–240 (1979).
M. Miller et al., Chem. Res. Toxicol., vol. 4, No. 3, pp. 324–329 (1991).
G. Galfre et al., Methods in Enzymology, vol. 73, pp. 3–47 (1981).
D. Kabakoff, Enzyme–immunoassay. Immunoenzyme Technique, Chapter 4, CRC PRess (1980).
Technnology, "Scientific Swapping, Onsite Analytical Technology uses Medical Technology to Dectect Organic Content", Kimberly A. Roy, 4 pages.
On Site News, "Field Analysis Using Rapid Immunoassay Screens", Aisling Scallen, Kevin Carter and Alan Staple, 2 pages.
"Immunoassay Technology for On–Site Testing", Kevin R. Carter, 2 pages.
Pollution Engineering, "On–Site Screening Speeds Sample Analysis", Kevin R. Carter, Mar. 15, 1992, 36–38.
American Chemical Society, "Monoclonal Antibody Technology Program", Stephen Krogsrud and Kenneth T. Lang, 1990, 21–26.
American Cancer Society, "General Motors Cancer Research Foundation Awards, Monoclonal Antibodies" Cesar Milstein, Ph.D. FRS, vol. 49, May 15, 1982, 1953–1957.
The Journal Of Histochemistry And Cytochemistry, "Peroxidase–Labeled Antibody a New Method of Conjugation", Paul K. Nakane and Akira Kawaoi, vol. 22, No. 12, 1084–1091.
Introduction And General Principles, William D. Odell, 1–13.
History And Future Outlook Of Enzyne Immunoassay, Eva Engvall, Ph.D., 1–3.
Methods In Enzymology, "Principles and Methods", vol. 70, 104–142.
"Enzyme Mediated Immunoassay: An Overview", Department of Developmental and Cell Biology University of California, T. T. Ngo, 3–32.
Petroleum Contaiminated Soils, vol. 2, "Analysis of Petroleum Contaminated Soil and Water: An Overview", Edward J. Calabrese and Paul T. Kostecki, 96–109.
Petroleum Contaminated Soils, vol. 2, "Field–Screening Tehniques: Quick and Effective Tools for Optimizing Hazardous Waste Site Investigations", Edward J. Calabrese and Paul T. Kostecki, 111–117.
Petroleum Contaminated Soils, vol. 3, "Relationships Between Chmical Screening Methodologies for Petroleum Comtaminated Soils: Theory and Practice", Edward J. Calabrese and Paul T. Kostecki, 93–109.
Immunochemical Methods For Environmental Analysis, "Antibodies", Helen Vunakis, 1–12.
Immunoassays For Trace Chemical Analysis "Rapid On–Site Immunoassay Systems, Agricultural and Environmental Applications", J. H. Rittenburg, G. D. Grothaus, D. A. Fitzpatrick, and R. K. Lankow; 28–39.
Immunochemical Methods For Environmental Analysis, "Immunoassay Methods", Jeanette M. Van Emon, 58–64.
Immunoassays For Trace Chemical Analysis, "Immunochemical Techniques in Trace Residue Analysis", Martin Vanderlaan, Larry Stanker, and Bruce Watkins, 2–13.

Primary Examiner—Mary E. Ceperley
Attorney, Agent, or Firm—Oblon, Spivak, McClelland, Maier & Neustadt

[57] ABSTRACT

An immunoassay method that integrates a sample processing component that enables the testing of samples for the presence of an immunologically non-remarkable compound, such as benzene, by the use of a monoclonal antibody having specific reactivity for an immunologically remarkable compound, such as nitrobenzene, which has been prepared by reacting the immunologically non-remarkable compound with derivatizing agent, and the components for performing the method, wherein one example of the immunoassay utilizes a monoclonal anti-nitrobenzene antibody to detect the presence or absence of benzene contamination in an aqueous sample when tested in a field or laboratory location.

39 Claims, 3 Drawing Sheets

IMMUNOASSAY METHOD FOR DETECTING AN IMMUNOLOGICALLY NON-REMARKABLE COMPOUND, ITS COMPONENTS AND A KIT FOR USE IN PERFORMING THE SAME

BACKGROUND OF THE INVENTION

1. Field of the Invention

The present invention relates to methods, compositions and kits for performing immunoassays to detect an immunologically non-remarkable compound, such as benzene.

2. Discussion of the Background

Testing is an essential, and integral, component of all environmental protection and restoration activities. It is the rate limiting element that influences the time, cost, and overall efficiency of project management.

The Environmental Protection Agency (EPA) has long promoted and supported the concept of screening methods to supplement laboratory analysis and increase overall efficiency. The need for more effective methods has been recognized in the Superfund Amendments and Reauthorization Act of 1986 which specifies the development and evaluation of alternative time and cost-saving methods that will assist in the eventual remediation of the nations Superfund sites.

Effective field screening methods can increase the efficiency of site management and improve overall data quality when used to supplement the services of regional laboratories. The development of these methods, however, requires a technology that will be compatible with numerous compounds and matrixes and yet be simple, effective and rugged enough to be incorporated into a protocol for use in the field.

Screening methods need to provide fast, simple, cost-effective and reliable information when operated under field conditions. The reagents and equipment should be portable and stable at ambient conditions, and the claims relating to performance should accurately reflect anticipated field use. The methods should be able to rapidly provide an ample quantity of data, and the protocol should be simple to perform and safe to use. Performance characteristics relative to sensitivity, freedom from matrix interferences and cross-reacting compounds, and correlation to an acceptable reference method should be carefully evaluated. Developers must maintain high, and consistent, quality standards relative to the consistency of their manufacturing protocols, the adequacy of in-process and pre-release quality control methods, and the reliability of their product claims. A necessary characteristic of particular significance for screening methods, is that they exhibit a very low frequency of false negative results.

Screening methods detect contamination at specified concentrations. The concentration may relate to a hazardous threshold, a clean-up target, or a process-control parameter. The potential implications of false negative data far outweigh those of false positive results. The consequence of a false positive, while a costly problem that needs to be minimized, results in additional testing or treatment. False negative data, however, provides an erroneous perception of a clean site, and may have serious environmental and legal consequences. Safeguards that minimize the incidence of false negative results are imperative. Appropriate control over the frequency of false positive data needs to be established and maintained.

Immunoassay methods combine the specific binding characteristics of an antibody molecule with a read-out system that is used to detect and quantify compounds. Current immunoassay technology benefits from the diversity of detection systems developed that use enzyme-catalyzed chromogenic reactions, radionuclides, chemiluminescence, fluorescence, fluorescence polarization and a variety of potentiometric and optical biosensor techniques. Improvements in the sensitivity achieved has necessitated the generation of new descriptive nomenclature for methods that can now detect "zeptomole" ($10^{-21}$ moles=600 molecules) concentrations.

The U.S. Environmental Protection Agency has concluded that immunoassay technology provides an advantage over the traditional analytical methods (gas chromatography (GC), gas chromatography/mass spectrometry (GC/MS), high performance liquid chromatography (HPLC) by increasing the sample throughput at a lower cost (Van Emon et al. in *Field Screening Methods for Hazardous Wastes and Toxic Chemicals*, p. 815–818 (1991)). The EPA SW-846 Organic Methods Work Group have approved draft immunoassay methods for inclusion into the next revision of the SW-846 methods and for use in a variety of environmental testing applications. From this information it is obvious that newly developed reagents and immunoassays have become acceptable analytical tools for the environmental field.

Benzene is a carcinogenic environmental contaminant. Federal and state regulations have been promulgated to curb further benzene pollution and to aid in the remediation of previously contaminated sites. An effective immunoassay for the detection of benzene would dramatically assist in this effort by facilitating site characterization, remediation and monitoring activities.

The technical challenges associated with producing an immunoassay method for benzene, however, are significant. Benzene is an unremarkable monocyclic aromatic molecule that is structurally a component of many other compounds found commonly in nature. For example, the amino acid phenylalanine is a constituent of virtually all proteins and contains a phenyl group similar in conformation to benzene. An immunoassay that used an antibody that would bind to benzene would suffer from significant interference caused by the binding to structurally related compounds in the sample. The production of an antibody to benzene could also prove difficult since the stimulation of the immune response to benzene, and an antibody cross-reactive with phenylalanine may result in an autoimmune-induced pathogenic reaction within the host animal.

Peck, PCT Application WO 88/09798, discloses an immunoassay for aromatic ring containing compounds, including toluene, toluidine, benzene, styrene, etc. However there is no discussion of how to provide a monoclonal antibody which will detect the presence of benzene, without detecting toluene or other similar aromatic compounds.

Ligler et al., U.S. Pat. No. 5,183,740, disclose a method and apparatus for performing immunoassays. In particular, Ligler et al disclose several specific assays for detecting nitrated compounds such as dinitrophenol and trinitrotoluene, but no mention of an assay which allows detection of benzene, by way of nitrobenzene, without interference due to cross-reactivity with closely related compounds such as nitrotoluene.

Thus, an immunoassay method is needed which will provide reliable accurate and fast results in the field for detection of immunologically non-remarkable compounds, such as benzene. Such an assay would increase the efficiency of environmental site management activities such as characterization (mapping), remediation monitoring, and regulatory compliance.

SUMMARY OF THE INVENTION

Accordingly, one object of the present invention is to provide an immunoassay for selective detection of an immunologically non-remarkable compound.

A further object of the present invention is to provide a monoclonal antibody for use in an immunoassay for the selective detection of an immunologically non-remarkable compound.

A further object of the present invention is to provide an immunogen which elicits a monoclonal antibody for use in an immunoassay for selective detection of an immmunologically non-remarkable compound.

A further object of the present invention is to provide an immunoassay kit for use in selectively detecting an immunologically non-remarkable compound.

A further object of the present invention is to provide a benzene immunoassay method which is field compatible, fast and accurate.

A further object of the present invention is to provide a benzene immunoassay method which gives minimal false negative results.

Another object of the present invention is to provide a benzene immunoassay method which detects benzene selectively with essentially no interference from closely related compounds, such as toluene or xylene.

Another object of the present invention is to provide an immunoassay method which allows the effective detection of an immunologically non-remarkable molecule, such as benzene, by the use of a monoclonal antibody having highly specific reactivity with an immunologically remarkable molecule, such as nitrobenzene, which is prepared by reaction of the immunologically non-remarkable molecule with a derivatizing agent, without interference from other closely related compounds having the same type of derivatization.

Another object of the present invention is to provide a benzene immunoassay which is simple to perform and easy to interpret in a field or laboratory setting by operators inexperienced in the art.

Another object of the present invention is to provide a monoclonal (MAb) antibody which is useful in the above-mentioned benzene immunoassay.

Another object of the present invention is to provide a monoclonal antibody with specific reactivity towards nitrobenzene having minimal cross-reactivity for other nitrated molecules which may be coderivatized during the nitration of benzene, such as toluene or xylene.

Another object of the present invention is to provide a reagent (e.g., an enzyme conjugate reagent) for use with the monoclonal antibody in competitive binding type immunoassays.

Another object of the present invention is to provide immunogens which elicit an anti-derivatized-benzene monoclonal antibody response.

Another object of the present invention is to provide a kit for performing a benzene immunoassay in water or soil samples.

Another object of the present invention is to provide a sample processing procedure for preparing samples from aqueous or soil matrix samples for use in the immunoassay of the present invention.

Another object is to provide a device for use in performing the sample processing procedure for preparing aqueous or solid matrix samples for use in the immunoassay of the present invention.

These and other objects of the present invention, which will become apparent from a reading of the description of the invention given hereinbelow, have been found by the inventors to be satisfied by their discovery of a monoclonal antibody which selectively binds an immunologically remarkable compound, such as nitrobenzene, which has been prepared by reaction of an immunologically non-remarkable compound, such as benzene, with a derivatizing agent, such as a nitrating agent, the inventors' discovery of immunogens which can be used to generate such a monoclonal antibody, the use of such an antibody in an immunoassay for detecting the immunologically non-remarkable compound, and a sample processing protocol which concentrates and converts the immunologically non-remarkable compound in a sample to the immunologically remarkable compound for reaction with the monoclonal antibody.

The present invention accordingly provides, among its varied embodiments, both an antibody and a test kit which incorporates the antibody. The kit is useful to detect the presence of the immunologically non-remarkable compound in an aqueous or soil matrix sample by the use of a sample processing protocol which converts the immunologically non-remarkable compound in the sample to the immunologically remarkable compound and recovers the immunologically remarkable compound in an immunoassay compatible matrix for detection using the antibody, and thereby provides an easy-to-use and highly reliable kit for environmental testing applications.

BRIEF DESCRIPTION OF THE FIGURES

A more complete appreciation of the present invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

Figure 1:
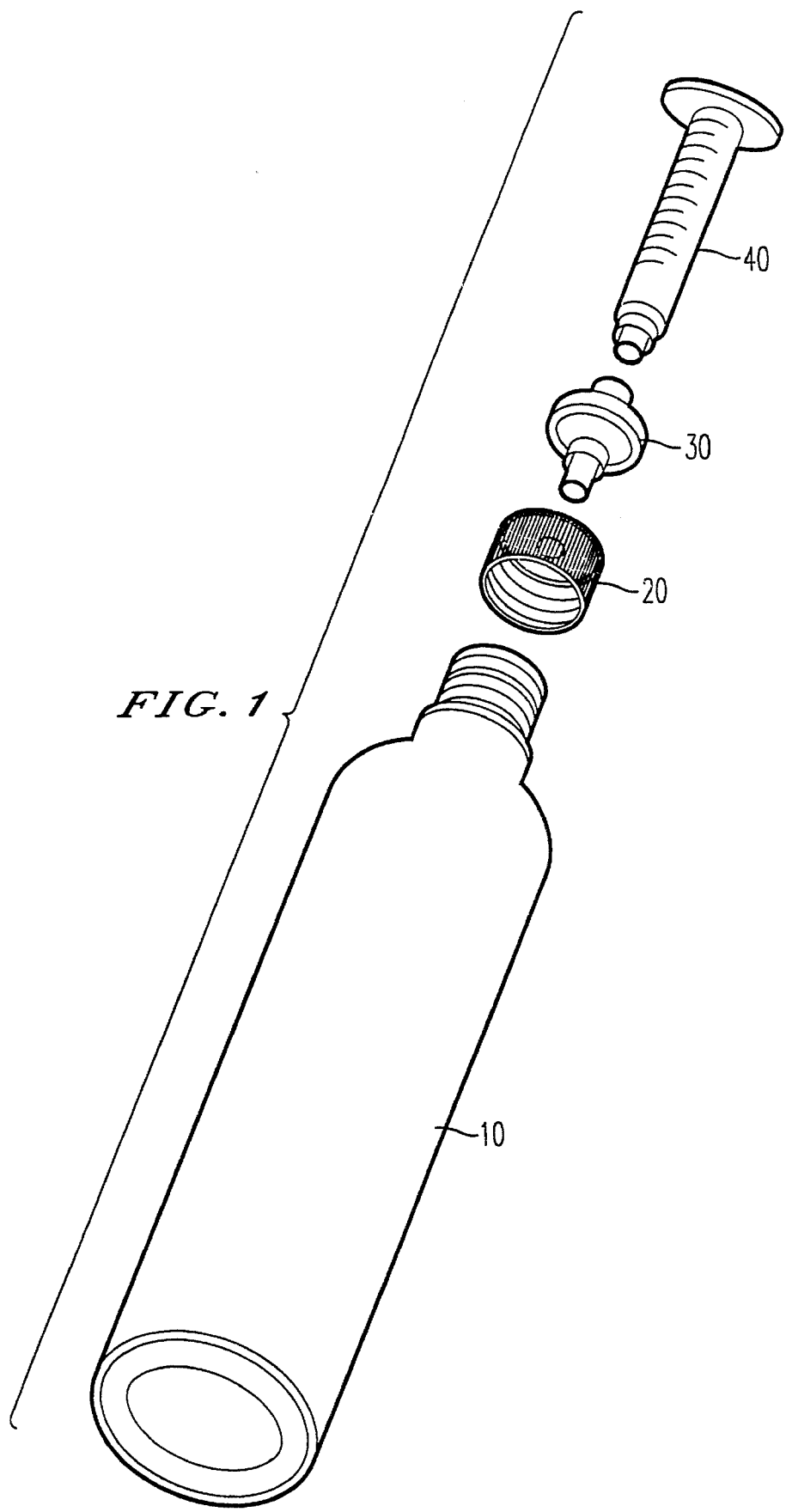
FIG. 1 shows a suitable extraction vessel for use in the first extraction step of the sample processing protocol of the present invention, showing the flexible extraction vessel (10), extraction vessel cap (20) which optionally contains glass wool, optional water-impermeable filter (30), and sample collection tube (40).

The present invention relates to a monoclonal antibody, immunogen for preparing the monoclonal antibody and reporter molecule reagent cross-reactive with the monoclonal antibody for use in an immunoassay method for the detection of an immunologically non-remarkable compound. Within the context of the present invention, the term "immunologically non-remarkable compound" refers to a compound which would suffer from high levels of interference during reaction with a monoclonal antibody designed to bind to the immunologically non-remarkable compound, due to the abudance of similarly structured compounds commonly found in an environmental testing sample or in nature. In other words, the immunologically non-remarkable compound has no particular distinguishing feature which would allow the selective recognition and binding of a monoclonal antibody directly to the immunologically non-remarkable compound, without significant interference from structurally similar compounds. Examples of such immunologically non-remarkable compounds include benzene (as described in the background section above), naphthalene, aliphatic hydrocarbons such as methane, ethane or propane, individual polyaromatic hydrocarbons such as anthracene,.

Conversely, the term "immunologically remarkable compound", as used in the present invention, relates to a compound which has an immunologically functional substituent which, in effect, provides a "handle" or differentiator for a monoclonal antibody to selectively detect the immunologically remarkable compound in the presence of structurally similar compounds present in the sample. In the present invention, the immunologically remarkable compound is prepared by reaction of the immunologically non-remarkable compound of interest with a derivatizing agent.

The derivatizing agent used may be any agent which provides to the immunologically non-remarkable compound, an immunologically functional substituent as described above. For example, if benzene is the immunologically non-remarkable compound of interest, one may use a derivatizing agent, such as a nitrating agent, sulfonating agent, methylating agent, acylating agent or halogenating agent, to prepare a benzene derivative (the immunologically remarkable compound), such as nitrobenzene, chlorobenzene, etc., which allows detection by a monoclonal antibody having specific reactivity for the benzene derivative. Thus, by detecting the presence of the immunologically remarkable molecule, one obtains a method for detection of the immunologically non-remarkable molecule.

In a preferred embodiment, the present invention provides an immunoassay for determining the presence of benzene contamination in a sample (suspected to contain benzene). The immunoassay comprises:

(i) processing the sample using a sample processing protocol to concentrate and convert benzene in the sample into a derivatized benzene, such as nitrobenzene, and recover the derivatized benzene in a suitable immunoassay compatible solvent;

(ii) contacting a monoclonal antibody with specific reactivity towards the derivatized benzene (such as nitrobenzene) with a mixture of the processed sample and a reporter molecule reagent which is cross reactive with the monoclonal antibody, to form an assay mixture;

(iii) incubating the assay mixture to allow competitive binding to the antibody between the derivatized benzene, if present, in the processed sample and the reporter molecule reagent to form a monoclonal antibody complex; and (iv) detecting the extent of binding of the reporter molecule reagent to the monoclonal antibody and correlating the amount of bound reporter molecule reagent to the amount of derivatized benzene in the processed sample, which correlates to the amount of benzene in the sample.

The phrase "specific reactivity towards" as used herein signifies the ability of the monoclonal antibody of the present invention to preferentially bind the immunologically remarkable compound of the present invention, without significant interference from other structurally and/or functionally similar compounds present in the sample. As an example, the monoclonal anti-nitrobenzene antibody of a preferred embodiment of the present invention will preferentially bind nitrobenzene, even in the presence of such closely related compounds as nitrotoluene and nitroxylene, preferably with less than 50% cross-reactivity with the closely In another embodiment, the invention provides an immunoassay kit which comprises four basic components: (1) a sample processing means for concentrating and converting benzene in an aqueous or soil matrix sample into a derivatized benzene, such as nitrobenzene, in a solution suitable for immunoassay; (2) a monoclonal antibody with specific reactivity towards the derivatized benzene; (3) a reagent cross reactive with the monoclonal antibody and susceptible to detection, and optionally (4) a signal-generating reagent.

Throughout the present description, the present invention will be described with respect to detection of benzene by way of a monoclonal antibody having specific reactivity for nitrobenzene. This is merely for exemplary purposes only and is in no way intended to be limiting on the present invention. The preferred structures of the immunogen and reporter molecule reagent of the present invention are also applicable to their use in preparing an immunoassay for detecting derivatives of other non-remarkable compounds by merely substituting the appropriate derivatizing group (such as Cl, Br, I or $SO_4H$) for the nitro group of the preferred embodiment and substitution of the particular non-remarkable skeleton (such as naphthyl) for the phenyl ring of the immunogen or reporter molecule reagents described below.

To induce, in a host, the formation of the present monoclonal antibodies that can be used to detect benzene, an immunogen is used which contains a derivative moiety which mimics the structural features of derivatized benzene. The immunogen is synthesized, by standard methods, by coupling a derivative moiety to an immunologic carrier molecule.

Examples of suitable methods for coupling a derivative moiety to an immunologic carrier molecule have been described in co-pending U.S. applications Ser. Nos. 07/984, 098, 08/068,093 and 08/097,223 to Friedman et al, which are hereby incorporated by reference.

Known immunological carrier moieties can be used, including albumin (e.g., bovine serum albumin), thyroglobulin (e.g., bovine thyroglobulin), hemocyanin (e.g., keyhole limpet hemocyanin), polyamino acids (e.g., polylysine) and other molecules having a minimum size, complexity, and foreignness to the host animal. Carriers are usually of the class of proteins, polypeptides or peptides having a molecular weight of at least 1,000 daltons and preferably >10,000 daltons. Carrier molecules may have a reactive group(s) available for covalent conjugation of the derivative. R-groups (e.g., COOH, $NH_2$) of amino acids or sugar moieties of glycoproteins are often used for this purpose in the synthesis of immunogens. Preferably, the immunogen is a compound of the formula

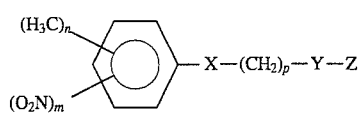

wherein

X and Y are each, independently

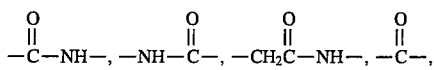

—NR$^1$—, —S— or —O—; —NR$^2$—NR$^3$—; or a single bond, or X is

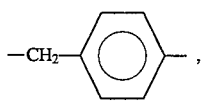

—COO—, wherein R$^1$-R$^3$ are each independently selected from the group consisting of H, C$_1$–C$_2$ alkyls, and linear, branched and cyclic C$_3$–C$_6$ alkyls;

n is 0 or 1;

m is an integer from 1 to 3;

p is 0 or an integer from 1 to 4;

linked to an immunogen carrier molecule Z;

where Z is an immunologic carrier molecule and the rest of the molecule is the derivative moiety of the immunogen.

A most preferred immunogen is

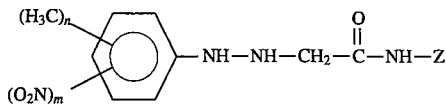

Small environmental chemicals, such as nitrobenzene, by themselves are too small to directly stimulate an immune response and elicit an antibody response. To elicit an antibody response, such small molecules are derivatized to attach a chemical bridge that is able to subsequently bind to a much larger "carrier" molecule prior to immunization. According to one embodiment of the present invention, the small molecules and accompanying bridge structures of the derivative are designed so that they immunologically mimic nitrobenzene. A number of modifications to the bridge structure (X—(CH$_2$)$_n$—Y) are possible and produce similar results. Any vertebrate is a suitable host for the immunization procedure, such as mice, rats, dogs, pigs and other domestic animals, with mice being preferred. Alternatively, in vitro immunization or recombinant DNA methods may be used.

The immunoassay method of the present invention uses a hybridoma-derived monoclonal antibody. The monoclonal antibody is selected using a multi-parameter screening process. A reactive panel profiling system is developed to identify appropriate cell lines and monoclonal antibodies on the basis of sensitivity for nitrobenzene and freedom of interference from confirmed negative soil samples or cross-reacting compounds. The monoclonal antibody binds selectively to nitrobenzene with minimal cross-reactivity with closely related nitrated aromatics such as nitrotoluene, nitroxylenes or dinitrobenzene. The antibody allows the method to rapidly detect benzene contamination, at, or above, a concentration of 1 ppb in a 0.9 L aqueous sample, with lower concentrations detectable utilizing layer sample. The antibody operates through the selective recognition of a derivatized benzene, such as nitrobenzene, with little or no cross-reactivity with closely related derivatized aromatics, such as nitrotoluene or nitroxylene.

The reporter molecule reagent of the present invention, which in a preferred embodiment is an enzyme conjugate reagent, is cross reactive with the monoclonal antibody and capable of providing a detectable signal, either alone or in combination with one or more co-reagents. Preferably, the reporter molecule reagent comprises a compound of formula

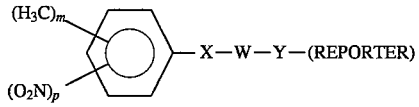

wherein

X and Y are each, independently

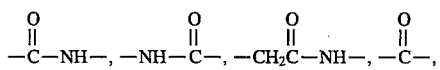

—CO—NH—NH—, —O—CH$_2$—CO—NH—NH—, —NR$^4$—, —CH$_2$S— or —O—; or a single bond, or X is

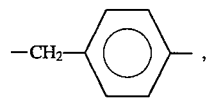

—COO—, wherein R$^4$ is selected from the group consisting of H, C$_1$–C$_2$ alkyls, and linear, branched and cyclic C$_3$–C$_6$ alkyls;

W is —C$_6$H$_4$— or —(CH$_2$)$_n$—;

n is 0 or an integer from 1 to 4, m is 0 or 1; and p is an integer from 1 to 3.

The reporter moiety used in the present invention may include an enzyme, a fluorescent compound, a chemiluminescent compound, a bioluminescent compound, a dyed latex particle or a radioactive atom. A preferred reporter moiety for use in the enzyme-conjugate reagent of the present invention includes an enzyme selected from the group consisting of horseradish peroxidase, alkaline phosphatase, glucose oxidase, β-galactosidase, glucose oxidase, G6-PDH (glucose-6-phosphate dehydrogenase) urease with horseradish peroxidase being most preferred.

A most preferred enzyme conjugate reagent is a compound of formula

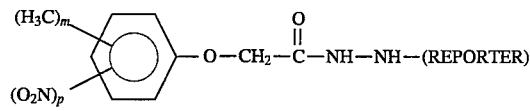

The enzyme conjugate is prepared using conventional methods such as those described in U.S. applications Ser. Nos. 07/984,098, 08/068,093 and 08/097,223 to Friedman et al.

The enzyme conjugate of the present invention is cross-reactive with the antibody of the present invention and capable of inducing a detectable change by reaction with a signal producing substrate(s) or reagent used in the immunoassay.

The immunoassay-based system of the present invention uses a signal producing reagent which, upon reaction with the bound enzyme conjugate/antibody complex after incubation, provides a detectable signal indicating the presence or absence of benzene contamination in the sample being tested. Suitable signal producing reagents for chromogenic immunoassays include a hydrogen peroxide/tetramethyl benzidine pair, or a hydrogen peroxide/phenylene diamine pair, in combination with an enzyme conjugate reagent containing horseradish peroxidase, o-nitrophenyl-β-D-galactopyranoside (ONPG) in combination with an enzyme conjugate reagent containing β-galactosidase, o-nitrophenylphosphate in combination with an enzyme conjugate reagent containing alkaline phosphatase, or glucose in combination with glucose oxidase or G6-PDH. The method of the present invention preferably uses the combination of a hydrogen peroxide ($H_2O_2$) substrate solution with a tetramethylbenzidine (TMB) chromogen, with the combination producing a blue chromophore upon oxidation of TMB by $H_2O_2$.

An important characteristic of the immunoassay of the present invention, as well as with any field screening method, is the minimization of false negative results without producing excessive false positive data. Statistically, therefore, the standard concentration should not be set at the detection concentration of interest, but below it. Setting the standard concentration to coincide with the regulatory concentration would result in a 50% false negative incidence. To minimize this effect, standards used in the immunoassay of the present invention are offset in concentration to produce a high confidence level of detecting contamination at, or above, the desired level. For example, to obtain a method which gives results having a high degree of confidence for detection of benzene at 5 ppb, a <5 ppb standard could be used.

The standard is set below the target level. The actual concentration of standard used is a function of the binding characteristics of the antibody and the overall precision of the method.

The present method is designed to test samples suspected of containing benzene contamination. However, in order to use the immunoassay of the present invention for assay of an aqueous sample, the aqueous sample must be processed into a sample which is compatible with the immunoassay chemistry and has a sufficient concentration of nitrobenzene to allow the present method to effectively detect benzene contamination at levels greater than 1 ppb in a 0.9 liter aqueous sample.

The sample processing protocol utilized in the present invention requires three basic steps:

(1) extraction of the aqueous sample with a water-immiscible extraction solvent to concentrate any benzene present in the sample into the water-immiscible extraction solvent, (2) nitration of the concentrated benzene-extraction solvent solution to convert the benzene to nitrobenzene, and (3) extraction of the nitrobenzene from the first extraction solvent into a second extraction solvent compatible with immunoassay chemistry.

One suitable method for sample preparation involves the following steps:

1. Combine the water sample with approximately 20% by weight of NaCl, based on the volume of water sample, in a flexible extraction vessel.

2. Extract the sample with a water-immiscible 1st extraction solvent in an amount such that the ratio of 1st extraction solvent to water sample is from 1:90 to 1:1000, preferably from 1:200 to 1:400.

3. Remove the 1st extraction solvent containing the extracted benzene and transfer it to a nitration vessel containing a nitrating agent.

4. Following nitration, to convert the benzene to nitrobenzene, remove the nitrated solution contained in the 1st extraction solvent and transfer to another extraction vessel containing a 2nd extraction solvent in a ratio of 2nd extraction solvent to 1st extraction solvent of approx. 1:10 to allow nitrobenzene to repartition.

5. Following the separation of the 1st and 2nd extraction solvent layers, the second extraction solvent, which now contains the nitrobenzene, is diluted 15–25 fold with an immunoassay medium to provide a sample for assay by the immunoassay of the present invention.

In the sample processing protocol of the present invention the flexible extraction vessel may be made from any flexible material which is compatible with the extraction components, and is preferably an inexpensive polystyrene or polyester bottle, most preferably one liter in size. When a one liter bottle is used it is preferred to add 900 ml of the water sample to the bottle along with 180 grams of sodium NaCl. Any sample volume can be used however, with higher sample volumes leading to a test with increased sensitivity. Increasing the amount of NaCl to 20% (w/v) improves the extraction of benzene from water to greater than 62%. Other salts which decrease the solubility of benzene in water may also be used, either alone or in combination. However, amounts higher than about 20% tend to provide only limited returns in extraction efficiency and suffer from solubility limits and the disadvantages of longer shake times needed to dissolve more salt.

When a 900 ml water sample is used, the first extraction solvent is preferably added in an amount of approximately 2.25–4.5 ml, most preferably approximately 3.5 ml. Any water-immiscible solvent having a high partition coefficient for benzene and compatible with the nitration chemistry, may be used as the 1st extraction solvent. Preferably, the 1st extraction solvent is a $C_1$–$C_6$ alkyl acetate or an aliphatic $C_5$–$C_{12}$ hydrocarbon solvent, most preferably iso-octane. Using the most preferred water:iso-octane ratio of 250:1, benzene is concentrated approximately 180 times into the iso-octane layer. Increasing the amount of 1st extraction solvent used increases the % benzene extracted but reduces the concentration factor in the solvent. Upon extracting the benzene from the sample into the 1st extraction solvent, the benzene-containing 1st extraction solvent solution is then readied for nitration.

In performing the nitration step, any nitrating agent which is compatible with the 1st extraction solvent may be used, with nitronium salts such as nitronium tetrafluoroborate (NTFB) being most preferred. The nitration reaction is performed by mixing the 1st extraction solvent solution with the nitrating agent at room temperature for a period of up to about 2 minutes, with 1 minute being preferred. An alternative nitration method when using a solid nitrating agent is to immobilize the agent on a support, such as a column or filter, and pass the 1st extraction solvent solution through the support.

Following the nitration reaction, the nitrobenzene in the solution is repartitioned into a 2nd extraction solvent, which is different from the 1st extraction solvent. The 2nd extraction solvent must have greater affinity for nitrobenzene than the 1st extraction solvent so that the nitrobenzene formed by the nitration reaction may be transferred into the 2nd extraction solvent. Polyethylene glycols are preferred as this 2nd extraction solvent, with PEG400 being most preferred. The resulting solution of nitrobenzene in the 2nd extraction solvent is then diluted 5–25 fold, most preferably 10–20 fold into a suitable immunoassay medium, such as PBS/Casein and the resulting diluted sample used as the assay sample in the immunoassay method of the present invention.

Using the sample processing steps of the present invention, a 5 ppb benzene in water sample will result in a concentration of 900 ppb benzene in iso-octane. Nitration of this solution is essentially 100% efficient. The added mass of the nitro group means that a 900 ppb benzene solution makes a 1350 ppb nitrobenzene solution. The PEG400 extraction step has been shown to result in at least an additional 5-fold increase in concentration. Therefore, a 1350 ppb nitrobenzene solution becomes a 6750 ppb nitrobenzene in PEG400 solution. If this solution is diluted 1:20 and then introduced into the immunoassay, the concentration of the nitrobenzene in the immunoassay will be about 320 ppb. Therefore, the immunoassay to be used with the present sample processing protocol should have sufficient sensitivity to detect at least 320 ppb of nitrobenzene in the presence of PEG400.

In performing the first extraction step of the sample processing protocol, it has been found to be advantageous to utilize a flexible extraction vessel equipped with a cap to which is affixed a volumetric sample collection means, such as a syringe barrel (See FIG. 1). Following thorough mixing of the aqueous sample and the first extraction solvent, the cap (20) having a sample collection means (40) attached is placed onto the extraction vessel (10), the extraction vessel (10) is compressed to force the benzene-containing isooctane layer up into the sample collection means (40). In some water samples obtained from lakes and ponds, an emulsion is sometimes formed. If an emulsion forms from a particular sample, the emulsion can be removed by the use of a small plug of glass wool in the solid cap of the extraction vessel or through the use of an antifoam agent such as Antifoam 289 or Antifoam 203, available from Sigma, or Dytek A, available from Dupont.

As a further improvement, a water-impermeable filter (30) may be placed between the extraction vessel cap (20) and the sample collection means (40) in order to avoid the passage of water into the sample collection means (40). Once the sample has been collected in the sample collection means (40), the sample may be then transferred to the nitration vessel to carry on the sample processing protocol above.

In addition to the test for aqueous samples described above, this method is designed to also test solid matrices. However, the testing of solid matrices requires that the issues of sample collection, dispersion, extraction and clarification be addressed and integrated with the immunoassay component.

While the assay of the present invention may be performed on samples of a wide range of qualities, a reproducible, particulate-free, extract is preferred for optimum results. The extraction and recovery of a compound from soil requires the selection of an appropriate solvent system, adequate sample dispersion, sufficient time for partitioning, non-invasive clarification and compatibility with the subsequent immunochemistry. However, current sample processing by analytical methods utilizes solvents that are incompatible with immunochemical methods and is slow and expensive.

One suitable method for soil sample preparation involves the collection of a 10 g sample measured with a small battery-operated balance. The sample is then transferred into a dispersion vial containing a suitable organic solvent, such as isooctane, and conventional dispersing pellets, and is subjected to a one minute manual agitation for adequate dispersion and partitioning of the analyte into the solvent. Filtration of the sample suspension to produce a particulate-free extract can be accomplished using a fingertip-operated filter unit fitted with non-adsorbing filters. The clarified extract is then ready for testing with the immunoassay of the present invention following derivatization and repartitioning as described above for aqueous samples, after their extraction with the 1st extraction solvent.

Buffers, detergents (e.g. Tweens, Tritons, etc.) or solvents, used alone, or in combination, have proven to be effective for extraction from soil samples. Analytical methods for the analysis of solid waste rely upon gravimetrically collected samples, and results are reported in gravimetric units. Volumetric sampling for solid waste should preferably be avoided because of the potential bias (up to 200%) that may be caused by the specific gravity of the sample.

The present immunoassay method is preferably for screening purposes and several safeguards have been incorporated to minimize the incidence of false negative results.

The basic characteristics of specificity and sensitivity of the assay of the present invention are a result of the monoclonal antibody (MAb) and the reporter molecule reagent. The assay provides highly selective recognition of nitrobenzene, low cross-reactivity with structurally similar aromatic compounds and is not significantly affected by normally found constituents of negative soil extracts, such as humic acid and fulvic acid.

Conventional hybridoma techniques are employed to prepare the anti-nitrobenzene monoclonal antibody (MAb) for the assay of the present invention, by the use of the immunogen reagent of the present invention. The method for producing MAbs is extremely powerful and allows for the preparation of a defined and reproducible Ab reagent. Hybridoma technology permits one to explore the entire antibody producing b-lymphocyte repertoire of the immune system and to select unique antibody producing cells that produce antibodies having unique binding characteristics. The production of polyclonal antisera is much less controlled since polyclonal antisera contain numerous Ab populations each having varying specificity and sensitivity characteristics that are the products of numerous responding b-cell clones. MAb reagents are also homogeneous with a defined specificity, unlike polyclonal antisera which contain a mixed population of antibodies. The use and appropriate selection of hybridoma cell lines provides MAb reagents that offer unique performance characteristics to the test system and consistency of the methods that utilize them.

A unique strategy is used for antibody production. This strategy involves developing an antibody to nitrobenzene which has negligible cross-reactivity with closely related compounds such as nitrotoluene or nitroxylene. The immunogen of the present invention is used to immunize suitable hosts, such as mice.

Hosts responding to the immunization protocol are selected as splenocyte (or lymphoid cell) donors for hybridoma production. A culture of immune lymphocytes fused with modified myeloma cells, using PE6 with modified myeloma cells in a defined tissue culture medium, such as HAT (hypoxanthine, aminopterin, thymidine), is capable of providing a variety of fusion products, such as s-s, s-m, and m-m (with s=splenocyte and m=myeloma cell). Within the tissue culture medium the s-s fusion product normally has a short lifetime and dies within days. Also, the m-m fusion product has a very short lifetime in the tissue culture medium used, lacking the metabolic components needed for DNA synthesis. However the s-m fusion product (or hybridoma) survives in tissue culture and retains the Ab-producing characteristics of the splenocyte parent, and the high rate of growth and relative immortality of the myeloma cell parent. These hybridoma cell lines replicate readily in culture producing daughter cells that provide a reproducible, homogeneous, and consistent supply of the monoclonal antibody of the present invention. Selection of the appropriate cell line provides the monoclonal antinitrobenzene antibody of a preferred embodiment of the present invention.

The structure of the reporter molecule reagent can have a significant influence on immunoassay performance. Both the small molecule portion and the bridge structure of the derivative play an important role in antibody binding. Antibody and report molecule reagent pairs should be able to satisfy the following criteria:

Antibody recognition and reporter molecule reagent displacement and prerequisite sensitivity for nitrobenzene, derived from benzene contaminants in a sample.

Low cross-reactivity of the antibody to non-related and functionally and structurally related compounds Insignificant negative soil matrix effects on binding of the reporter molecule and antibody.

Antibody and reagent pairs which best satisfy the above criteria are most suitable for the assay of the present invention.

The immunoassay of the present invention is performed according to the following procedure. Monoclonal antinitrobenzene antibody is provided in an assay vessel, preferably immobilized in the assay vessel or other solid support, preferably to the bottom of a polystyrene tube or microtiter plate, at a concentration, of from 0.005 to 20 µg/vessel. The concentration and affinity of the antibody for the sample molecules and reporter reagent molecules directly influences the overall sensitivity of the final method. High, equivalent, affinity, and minimal non-specific signal generation, produces assays having superior sensitivity, with affinity binding constants, Ka, from $10^4$–$10^{12}$ L/mol, preferably $10^5$–$10^{11}$ L/mol for the target analyte and reporter molecule.

The assay of the present invention compares the signal generated from a sample to be tested with the signal generated from a standard solution containing a derivatized benzene, such as nitrobenzene, which is present in the standard solution in an amount sufficient to provide a high confidence level for detection at the desired level.

By way of example, the following describes a simultaneous test of a negative sample, a sample containing >5 ppb of benzene, and a standard solution containing the equivalent of approximately <5 ppb of nitrobenzene. Initially, following extraction from the aqueous sample and concentration according to the sample processing protocol of the present invention, the samples and standard are added to separate, and identical, antibody-coated test tubes. To each tube is added an equal volume of the reporter reagent solution. The tubes are then allowed to incubate at ambient conditions for approximately ten minutes.

During the incubation period sample molecules and reporter reagent molecules compete for the limited number of antibody binding sites that are available on the bottom of each of the tubes. The antibody concentration present is insufficient to permit the binding of all of the sample and reporter reagent molecules simultaneously, and a situation somewhat analogous to the game of musical chairs exists, with the limited antibody binding capacity of the antibody molecules serving as the chairs in this example. The concentration of reporter reagent bound to the immobilized antibody in each tube after incubation is inversely proportional to the concentration of nitrobenzene in the processed sample or standard. The standard in the Standard tube limits the amount of the reporter reagent bound in the tube, the Negative sample permits more reporter reagent to bind (relative to the standard), and the positive sample permits less of the reporter reagent to bind (relative to the standard). At the end of the 10 minute incubation period, the tubes are washed leaving only the reagent that was retained by the immobilized antibody on the bottom of each tube.

The bound reagent/antibody complex remaining in each vessel or tube is next used to produce a detectable signal. Upon addition of a signal forming reagent(s), preferably a substrate/chromogen reagent pair, the enzyme molecule catalyzes the formation of a detectable signal. The signal that is generated is directly proportional to the concentration of reporter reagent present. A preferred substrate/chromogen reagent pair is $H_2O_2$ and tetramethylbenzidine (TMB) which, when used with the preferred reporter reagent wherein the reporter molecule is the enzyme HRP (horseradish peroxidase), reacts with the enzyme portion of the reporter reagent, which facilitates the oxidation of TMB by $H_2O_2$ and generates a blue color.

Thus, the negative sample tube rapidly produces a solution that is visibly darker (i.e. greater absorbance) than the standard tube. The positive test sample produces a solution having less color (i.e. lower absorbance) than the standard tube. By comparing the signal of the sample tubes to the signal of the standard tube using a battery-operated comparative photometer, optionally included with the kit of the present invention, samples containing greater than or equal to the desired level of contamination can be detected with ≧95% confidence. In this competitive ELISA method the final absorbance is inversely proportional to the analyte concentration present in the test sample.

The assay method of the present invention can process multiple samples in less than 30 minutes. The method is self-contained, field-compatible and does not require refrigeration. The detection level can be set at the users discretion, for example by dilution of the sample extract with great latitude in sensitivity provided by the sample concentration step.

The kit of the present invention contains five basic components: (1) a sample processing component for preparing the sample for testing by the assay method (described above), (2) at least one assay vessel, preferably a plurality, each containing an equivalent amount of the monoclonal antibody of the present invention, preferably immobilized, (3) a standard solution containing the equivalent of less than the target detection level, preferably from 50–95% of the target detection level of a derivatized analyte, such as nitrobenzene, in a suitable carrier, (4) a reporter reagent which is reconstituted to form a solution containing a reporter reagent which is cross-reactive with the monoclonal antibody, in a suitable carrier, where the reporter reagent is preferably a lyophilized enzyme-conjugate reagent, and (5) means for forming and detecting a signal indicating the presence or absence of the derivatized analyte, such as nitrobenzene, and thus the analyte of interest, such as benzene, contamination in the sample being tested. Optionally, the kit contains one or more of the following additional components: (6) wash solutions for performing the wash step of the assay method, (7) one or more dilution vials, and (8) stop solution to halt signal formation by the signal-forming reagent. Preferably the assay is provided in a format in which the means for forming and detecting a signal comprises the use of a substrate/chromogen reagent pair which forms a detectable colored signal with the level of nitrobenzene contamination (which correlates to benzene contamination) determined by comparison of the color developed by the test samples to the color of the kit standard.

In order to eliminate temperature variations, timing errors and operator mistakes, the standard is preferably run in parallel with the samples. Therefore, any assay variations will equally affect both the standard and the samples. Using this format with the standard run in parallel, the assay has the following characteristics:

1. The test can detect $\leq 1$ ppb of benzene in a 0.9 L aqueous sample.
2. The test is reproducible from lot-to-lot, day-to-day, and person-to-person.
3. The assay is operable over a temperature range of 4°–37° C.
4. Storage at ambient temperature (up to 30° C.) is acceptable.

The immunoassay of the present invention has many advantages, including field screening compatibility, speed in obtaining a result, and a lack of false negative results. Specific characteristics had to be integrated into the method in order to achieve these advantages. The first was a sample processing component to provide a concentrated assay-compatible sample for use in the assay of the present invention. The second was to minimize the incidence of false negative results. A false negative test result indicates the absence of contaminants in a sample having analyte present at or above the concentration of interest and therefore, can be potentially dangerous both to the customer and the environment. A false positive, which indicates contaminates when none is present, on the other hand, might be inconvenient but not dangerous. Therefore, a preferred immunoassay of the present invention is designed to detect positive aqueous samples containing benzene with a minimum of false negative results. This is accomplished by using a standard containing the equivalent of nitrobenzene in water at less than the target concentration of benzene. Preferably, two standards are run with each assay to provide an internal quality control parameter indicating the competency of the operator and the integrity of the chemistry.

The immunoassay has also been simplified by making it a semiquantitative test using a standard at a single concentration. The use of one standard concentration greatly simplifies the test protocol and eliminates the data manipulation and expensive instrumentation that are normally necessary for quantitative tests. The test becomes a semiquantitative "yes/no" test that determines whether a soil sample contains greater or less than a target level of benzene contamination. The use of multiple standards at varying concentrations could be used to allow one to perform a quantitative assay by interpolation of sample signal from the signal of a standard curve.

The immunoassay of the present invention makes possible the rapid screening of numerous samples in the field for benzene. The rapid, on-site screening of multiple samples is a significant advantage compared to the standard analytical GC methods. With the immunoassay method of the present invention, personnel, time and equipment can be used more cost-effectively.

Having generally described this invention, a further understanding can be obtained by reference to certain specific examples which are provided herein for purposes of illustration only and are not intended to be limiting unless otherwise specified.

EXAMPLES

EXAMPLE 1

Preparation of Assay components

Female Swiss Webster mice received a primary subcutaneous immunization with 50 ug of nitrobenzene derivatized to bovine thyroglobulin in adjuvant (MPL+TDM Emulsion, RIBI Immunochem Research, Inc., Hamilton, Mont.). Subcutaneous secondary injections (25 ug) were given at day 21, 35, and then monthly. The production of monoclonal antibodies was performed according to conventional procedures (see Milstein, *Cancer*, 49:1953–1957 (1982)). Hybridoma cultures producing monoclonal antibodies recognizing free hapten by EIA were cloned by limiting dilution. Clone F47-8H6 was selected based upon specificity, and interference criteria.

Horseradish peroxidase (HRP) conjugate reagent NAR 6 was prepared with a hydrazide derivative of nitrobenzene using the conventional periodate method (see Nakane et al J. Histochem. Cytochem. 22:1084 (1971)).

Antibody coated tubes

Antibody coated tubes were prepared by coating polystyrene (12×75 mm, NUNC) tubes with the monoclonal F47-8H6 antibody diluted in PBS and incubating overnight.

EXAMPLE 2

Immunoassay Procedure 900 ml of a water sample suspected of containing benzene was placed into a 1 L flexible plastic bottle equipped with a solid cap and containing 180 g of NaCl. After the addition of 3.5 ml of isooctane, the bottle was capped and shaken for 3 minutes. The solid cap was then replaced by a cap with a hole in the center, in which is inserted the tip of a 3 ml syringe barrel having a water impermeable filter interposed between the barrel and the bottle cap. The bottle was squeezed to force 2.4 ml of the isooctane solution layer into the syringe barrel, followed by transfer of the 2.4 ml of isooctane solution to a 4 ml glass vial containing 30 mg of nitronium tetrafluoroborate. The glass vial was then capped and shaken for 1 minute to effect nitration of benzene and other aromatics in the isooctane solution. 2.0 ml of the nitrated solution was transferred to a glass test tube containing 200 μl of PEG400 and the tube was agitated for 1 minute. 10 μl of the resulting PEG400 layer containing the nitrated products was then added to 200 μl of PBS/Casein containing HRP conjugate NAR 6. At the same time, 2×10 uL of the nitrobenzene standard were similarly added to PBS/Casein. The sample and the two standards were then poured into three identical antibody coated tubes, respectively, and the resulting solution mixed. The resulting solution was incubated for 10 minutes at ambient temperature and then washed 4× with a wash buffer (detergent-saline solution). 250 uL of tetramethylbenzidene solution (KP Laboratories, Cat. No. 50-76-02) was added along with 250 uL of hydrogen peroxide solution (KPL, Cat. No. 50-65-02) and the resultant solution mixed. After incubating for 2.5 minutes the color development reaction was stopped with 250 uL of stop solution (1M sulfuric acid).

The optical density (OD) of the test sample was compared to the OD of the nitrobenzene standard which was tested simultaneously with the sample. If the sample OD is less than the standard OD, the sample contains more than the standard concentration of benzene. If the sample OD is greater than the standard OD, the sample contains less than the standard concentration of benzene. Other concentration ranges can be assessed by diluting the test samples with suitable diluents, as long as they are non-reactive with the components of the assay.

Figure 2:
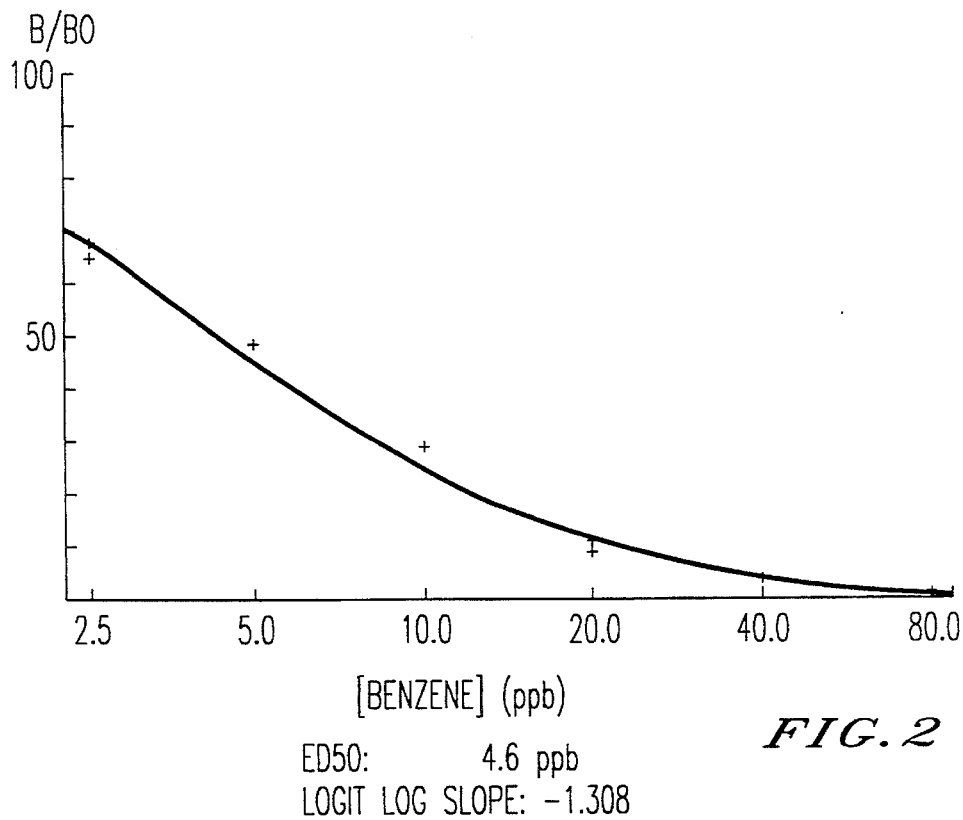
FIG. 2 provides the dose response curve for benzene in water using the present method.

To achieve a high level of confidence of benzene detection, the concentration of the nitrobenzene standard was determined by using a statistical approach. The standard was set at a point where the mean of the standard absorbance minus 2 standard deviations (SD) does not overlap the mean of the signal at the detection concentration. A dilution of the sample was used to reduce interference from methanol and to test at varying target concentrations. FIG. 2 provides the dose response curve for benzene in water using the method of the present invention.

The sensitivity of the present method was determined by spiking a confirmed negative water sample with benzene followed by assay using the method of the present invention.

Measurement of Matrix Interference in Negative Samples

Water samples obtained from local ponds, creeks and wells were analyzed by the standard protocol except that 4.5 ml of iso-octane was used in the extraction instead of 3.5 ml. The signal in the immunoassay was compared to a control and the B/Bo are shown below.

| Sample | B/Bo |
|---|---|
| iso-Octane control | 1.05 |
| Hope Valley Farms Pond | 1.03 |
| Umstead State Park | 1.06 |
| RDU Airport Run-Off | 1.00 |
| Water Garden Pond | 1.05 |
| EnSys Creek | 0.77 |
| Kirkwood Pond | 1.07 |
| Kirkwood Creek | 1.05 |
| Kirkwood Well | 1.08 |
| Northside (Durham) Influent | 0.61 |

Minimal matrix effects were seen using the assay of the present invention.

To determine the sensitivity of the test using the sample processing protocol and assay of the present invention, tap water was spiked with a benzene standard to obtain samples containing 0 or 80 ppb benzene in water. These samples were processed according to the sample processing protocol of the present invention. The samples were added to a protein A microtiter plate coated with Ab F47-8H6 (1:1000). Samples were incubated on the plate for 10 minutes and the plate was then washed 4 times with PBS/TX-100. Plates were developed with TMB/H202 for 4 minutes; stopped; and read at 450 nm. The results (see FIG. 2) indicate an $ED_{50}$ of 4.6 ppb benzene in water.

CROSS-REACTIVITY

Specificity with Other Potentially Cross-Reactive Compounds

Closely related nitro-aromatics were also evaluated for cross-reactivity in the benzene assay of the present invention.

Figure 3:
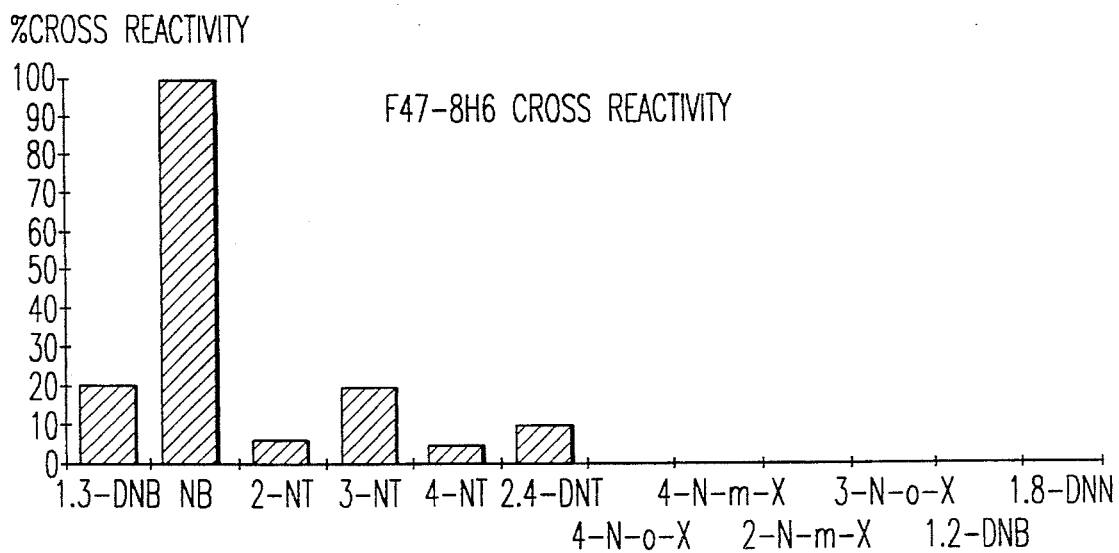
FIG. 3 shows the cross-reactivity characteristics of a monoclonal antibody of the present invention with other compounds which may be present in a sample.

The immunogen of the present invention was designed to elicit antibodies with the least amount of cross-reactivity towards relevant chemicals. It was predicted that the most significant cross-reactivity would be generated towards nitrotoluene compounds. Nitration of toluene has been shown to occur primarily in the 2 and 4-positions. The antibody reagent used in the assay of the present invention was highly specific for nitrobenzene with minimal cross-reactivity to 2-nitrotoluene, 4-nitrotoluene and other nitro-compounds (FIG. 3). FIG. 3 shows the cross-reactivity of compounds nitrated by a preferred embodiment of the present sample processing method. In FIG. 3: 1,3-DNB=1,3-dinitrobenzene; NB=nitrobenzene; 2-NT=2-nitrotoluene; 3-NT=3-nitrotoluene; 4-NT= 4-nitrotoluene; 2,4-DNT=2,4-dinitrotoluene; 4-N-o-X=4-nitro-o-xylene; 4-N-m-X=4-nitro-m-xylene; 2-N-m-X=2-nitro-m-xylene; 3-N-o-X=3-nitro-o-xylene; 1,2-DNB=1,2-dinitrobenzene; and 1,8-DNN= 1,8-dinitronaphthalene.

Figure 4:
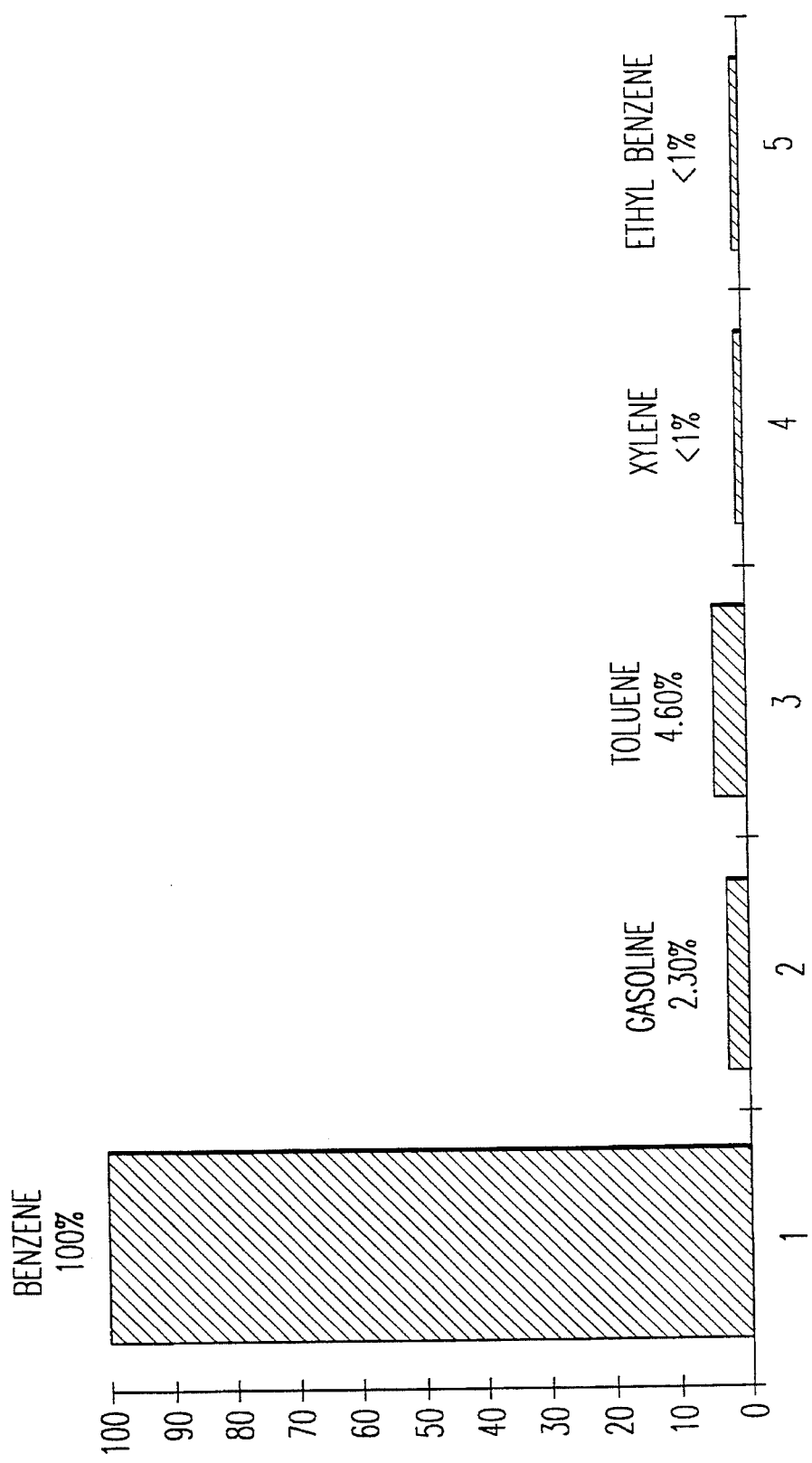
FIG. 4 shows the percent cross-reactivity of spiked water samples containing benzene, gasoline, toluene, xylenes and ethyl benzene. Each sample was extracted, nitrated and analyzed by the immunoassay of the present invention.

The compounds in Table I each showed <5% cross-reactivity using the sample processing and immunoassay method of the present invention. These results demonstrate that many similar nitroaromatic compounds, derived from nitration of aromatic compounds which are structurally similar to benzene and/or commonly found at benzene contamination sites, are not cross-reactive in the assay and will not affect the rate of false positive results except when they are present in excessively high concentrations. FIG. 4 shows the percent cross-reactivity of spiked water samples containing benzene, gasoline, toluene, xylenes and ethyl benzene. Each sample was extracted, nitrated and analyzed by the immunoassay of the present invention.

These results demonstrate that the assay is highly sensitive and specific for nitrobenzene and has little cross-reactivity toward other nitroaromatic compounds, thus allowing detection of benzene in the presence of other structurally similar aromatics such as toluene or xylene.

TABLE I

The following compounds showed less than 5% cross-reactivity with benzene. Cross-reactants were spiked into iso-octane, nitrated and extracted with PEG according to protocol.

m-Xylene
o-Xylene
p-Xylene
Creosote
1,2 Dichlorobenzene
Brake Fluid
100 Octane Fuel
JP4 Jet Fuel
Used Motor Oil
Methyl t-Butyl Ether
Trichloroethylene
2-methylpentane
n-Hexadecane
Etna Diesel
Acenapthene
Naphthalene
Crude Off-Shore Oil
Kerosene

TEMPERATURE SENSITIVITY

The benzene assay of the present invention can be operated at ambient temperatures.

The advantages of immunoassay technology can be attributed to the underlying lock and key binding principle and its compatibility with aqueous matrixes. This method does not require the chromatographic separation of sample components, nor does it require that compounds absorb visible, infrared or UV for detection. Interferences from other compounds are considerably less of a problem because of the conformational nature of the antibody binding process. Sample processing time is significantly reduced, and the direct testing of aqueous samples can be performed. The technology offers a unique, and conservative, approach to field screening. The incidence of false negative data is exceptionally low. Aspects that tend to interfere with immunoassay methods of this type tend to cause an overestimation of contamination, or false positive result by minimizing the binding of enzyme conjugate reporter molecule to antibody or suppressing signal generation by the enzyme.

This method offers significant versatility and performance advantages. It is a convenient and effective new tool that can enhance the efficiency of site management activities and the utilization of our national laboratory system.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A monoclonal antibody useful for the detection of an immunologically non-remarkable compound in a sample, wherein the monoclonal antibody has specific reactivity towards an immunologically remarkable compound prepared by reaction of said immunologically non-remarkable compound with a derivatizing agent, wherein said immunologically non-remarkable compound is benzene, wherein said derivatizing agent is a nitrating agent and said immunologically remarkable compound is nitrobenzene.

2. The monoclonal antibody of claim 1, wherein said antibody further has less than 20% cross reactivity with nitrotoluene.

3. The monoclonal antibody of claim 2, having less than 20% cross reactivity with natural soil constituents.

4. The monoclonal antibody of claim 1, obtained by
  (i) producing an immune response in a vertebrate host by immunization with an immunogen comprised of a derivative moiety of the formula

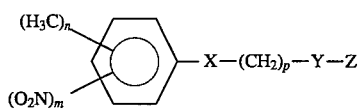

wherein
X and Y are each, independently

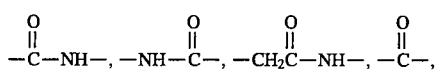

—NR$^1$—, —S—, —O—, —NR$^2$—NR$^3$— or a single bond; or X is

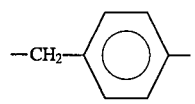

or —COO—; wherein R$^1$-R$^3$ are each, independently, selected from the group consisting of H, C$_1$-C$_2$ alkyls, and linear, branched and cyclic C$_3$-C$_6$ alkyls;
n is 0 or 1;
m is an integer from 1 to 3;
p is 0 or an integer from 1 to 4; linked to an immunologic carrier molecule Z;
  (ii) preparing a hybridoma from the lymphoid cells of said host;
  (iii) selecting said hybridoma to produce said monoclonal antibody; and
  (iv) obtaining said monoclonal antibody.

5. An immunoassay kit useful for detecting an immunologically non-remarkable compound in a sample, comprising a monoclonal antibody having specific reactivity towards an immunologically remarkable compound prepared by reaction of said immunologically non-remarkable compound with a derivatizing agent, and a sample processing means for converting said immunologically non-remarkable compound into said immunologically remarkable compound, wherein said immunologically non-remarkable compound is benzene, wherein said derivatizing agent is a nitrating agent and wherein said immunologically remarkable compound is nitrobenzene.

6. The immunoassay kit of claim 5, wherein said monoclonal antibody has less than 20% cross reactivity towards nitrotoluene.

7. The immunoassay kit of claim 5, wherein said monoclonal antibody has less than 20% cross reactivity towards natural soil constituents.

8. An immunoassay kit useful for detecting the presence of benzene in a sample, said kit comprising:
  (i) a sample processing means to concentrate and convert the benzene in the sample to nitrobenzene;
  (ii) a reaction vessel means containing an immobilized monoclonal antibody having specific reactivity towards nitrobenzene;
  (iii) a standard solution comprising nitrobenzene and a solvent;
  (iv) a reporter molecule reagent, which is cross-reactive with said monoclonal antibody; and
  (v) a means for causing said reporter moiety to generate a signal and a means for detecting said signal.

9. The kit of claim 8, wherein said sample processing means (i) further comprises a means for phase transfer of said nitrobenzene into a water-miscible solvent.

10. The kit of claim 8, wherein said standard solution comprises from 0.5 to 200 ppb of nitrobenzene.

11. The kit of claim 8, wherein said reporter molecule reagent is a compound of the formula

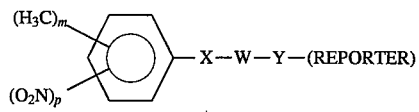

wherein
X and Y are each, independently $$-\overset{O}{\underset{\|}{C}}-NH-,\ -NH-\overset{O}{\underset{\|}{C}}-,\ -CH_2\overset{O}{\underset{\|}{C}}-NH-,\ -\overset{O}{\underset{\|}{C}}-,$$

—CO—NH—NH—, —O—CH$_2$—CO—NH—NH—, —NR$^4$—, —CH$_2$S—, —O— or a single bond; or X is

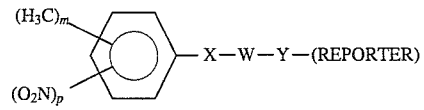

or —COO—; wherein R$^4$ is selected from the group consisting of H, C$_1$–C$_2$ alkyls, and linear, branched and cyclic C$_3$–C$_6$ alkyls;

W is —C$_6$H$_4$— or —(CH$_2$)$_n$—;

n is 0 or an integer from 1 to 4, m is 0 or 1; and p is an integer from 1 to 3, and (REPORTER) is a member selected from the group consisting of enzymes, fluorescent compounds, chemiluminescent compounds, bioluminescent compounds, dyed latex particles and radioactive atoms.

12. The kit of claim 11, wherein said reporter moiety is an enzyme selected from the group consisting of horseradish peroxidase, alkaline phosphatase, β-galactosidase, glucose oxidase, G6-PDH and urease.

13. The kit of claim 12, wherein said enzyme is horseradish peroxidase.

14. The kit of claim 8, wherein said reaction vessel means is a plurality of vessels, each containing an equivalent amount of said monoclonal antibody.

15. The kit of claim 8, wherein said reporter molecule reagent is a lyophilized reporter molecule reagent which is reconstituted prior to use.

16. The kit of claim 8, wherein said sample processing means comprises a water extraction vessel, a 1st extraction solvent immiscible with water, a 2nd extraction solvent different from said 1st extraction solvent and able to repartition nitrobenzene from said 1st extraction solvent into an aqueous matrix, and a nitrating agent.

17. The kit of claim 16, wherein said extraction vessel comprises a flexible vessel equipped with a cap, wherein said cap has affixed thereto a volumetric sample collection means.

18. The kit of claim 17, wherein said extraction vessel further comprises a water-impermeable filter interposed between said cap and said volumetric sample collection means.

19. The kit of claim 16, wherein said volumetric sample collection means is a syringe barrel.

20. The kit of claim 8, wherein said sample processing means comprises a dispersion vial, an extraction solvent and dispersing pellets.

21. An immunoassay for determining the presence of an immunologically non-remarkable compound in an aqueous sample, comprising:
(i) extracting said aqueous sample with a 1st extraction solvent to obtain a 1st extraction solvent solution;
(ii) submitting said 1st extraction solvent solution to a derivatization reaction using a nitrating agent, to obtain a derivatized solution;
(iii) extracting said derivatized solution with a 2nd extraction solvent to obtain an assay sample;
(iv) combining (iva) a monoclonal antibody with specific reactivity towards an immunologically remarkable compound prepared by reaction of said immunologically non-remarkable compound with said derivatizing agent, with (ivb) a mixture of (ivbi) the assay sample and (ivbii) a reporter molecule reagent which is cross reactive with said monoclonal antibody, wherein said reporter molecule reagent is susceptible to producing a detectable signal, to form an assay mixture;
(v) incubating said assay mixture to allow competitive monoclonal antibody binding between said immunologically remarkable compound, if present, in the assay sample, and said reporter molecule reagent;
(vi) causing production of said signal and correlating said signal to the amount of reporter molecule reagent bound to said monoclonal antibody to obtain a measure of the amount of said immunologically remarkable compound in said assay sample, which correlates to the amount of said immunologically non-remarkable compound in said sample, wherein said immunologically non-remarkable compound is benzene and said immunologically remarkable compound is nitrobenzene.

22. The immunoassay of claim 21, wherein said monoclonal antibody further has less than 20% cross reactivity with nitrotoluene.

23. The immunoassay of claim 21, wherein said monoclonal antibody is an immobilized monoclonal antibody.

24. The immunoassay of claim 21, wherein said monoclonal antibody is not immobilized.

25. The immunoassay of claim 8, wherein said reporter molecule reagent has the formula

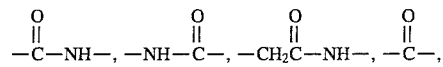

wherein

X and Y are each, independently $$-\overset{O}{\underset{\|}{C}}-NH-,\ -NH-\overset{O}{\underset{\|}{C}}-,\ -CH_2\overset{O}{\underset{\|}{C}}-NH-,\ -\overset{O}{\underset{\|}{C}}-,$$

—CO—NH—NH—, —O—CH$_2$—CO—NH—NH—, —NR$^4$—, —CH$_2$S—, —O— or a single bond; or X is

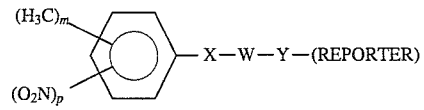

or —COO—; wherein R$^4$ is selected from the group consisting of H, C$_1$–C$_2$ alkyls, and linear, branched and cyclic C$_3$–C$_6$ alkyls;

W is —C$_6$H$_4$— or —(CH$_2$)$_n$—;

n is O or an integer from 1 to 4, m is 0 or 1; and p is an integer from 1 to 3, and (REPORTER) is a member selected from the group consisting of enzymes, fluorescent compounds, chemiluminescent compounds, bioluminescent compounds, dyed latex particles and radioactive atoms.

26. The immunoassay of claim 25, wherein said reporter moiety is an enzyme selected from the group consisting of horseradish peroxidase, alkaline phosphatase, β-galactosidase, glucose oxidase, G6-PDH and urease.

27. The immunoassay of claim 26, wherein said enzyme is horseradish peroxidase.

28. The immunoassay of claim 21, further comprising simultaneously assaying (1) a standard solution containing said immunologically remarkable compound and (2) said assay sample.

29. An immunoassay for determining the presence of nitrobenzene in a sample, comprising:
   (i) combining (ia) a monoclonal antibody with specific reactivity towards nitrobenzene, with (ib) a mixture of (ibi) the sample and (ibii) a reporter molecule reagent which is cross reactive with said monoclonal antibody, wherein said reporter molecule reagent is susceptible to producing a detectable signal, to form an assay mixture;
   (ii) incubating said assay mixture to allow competitive monoclonal antibody binding between nitrobenzene, if present, in the sample, and said reporter molecule reagent;
   (iii) causing production of said signal and correlating said signal to the amount of reagent bound to said monoclonal antibody to obtain a measure of the amount of nitrobenzene in said sample.

30. The immunoassay of claim 29, wherein said monoclonal antibody is an immobilized monoclonal antibody.

31. The immunoassay of claim 29, wherein said monoclonal antibody is not immobilized.

32. The immunoassay of claim 29, wherein said reporter molecule reagent has the formula

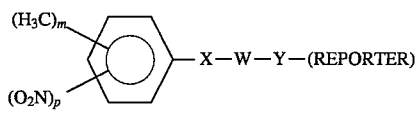

wherein

X and Y are each, independently

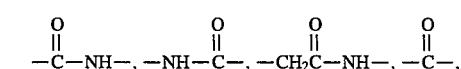

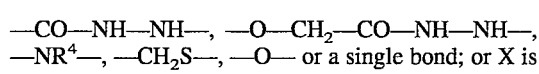

—NR$^4$—, —CH$_2$S—, —O— or a single bond; or X is

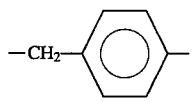

or —COO—; wherein R$^4$ is selected from the group consisting of H, C$_1$–C$_2$ alkyls, and linear, branched and cyclic C$_3$–C$_6$ alkyls;

W is —C$_6$H$_4$— or —(CH$_2$)$_n$—;

n is 0 or an integer from 1 to 4, m is 0 or 1; and p is an integer from 1 to 3, and (REPORTER) is a member selected from the group consisting of enzymes, fluorescent compounds, chemiluminescent compounds, bioluminescent compounds, dyed latex particles and radioactive atoms.

33. The immunoassay of claim 32, wherein said reporter moiety is an enzyme selected from the group consisting of horseradish peroxidase, alkaline phosphatase, β-galactosidase, glucose oxidase, G6-PDH and urease.

34. The immunoassay of claim 33, wherein said enzyme is horseradish peroxidase.

35. The immunoassay of claim 29, further comprising simultaneously assaying (1) a standard solution containing nitrobenzene and (2) said sample.

36. A method of using an immunogen to produce a monoclonal antibody with specific reactivity towards an immunologically remarkable compound prepared by reaction of an immunologically non-remarkable compound with a derivatizing agent, wherein said immunologically non-remarkable compound is benzene, wherein said derivatizing agent is a nitrating agent and said immunologically remarkable compound is nitrobenzene, said method comprising:
   (i) producing an immune response in a host with an immunogen capable of eliciting an immune response in a host to produce a monoclonal antibody with specific reactivity towards said immunologically remarkable compound;
   (ii) preparing a hybridoma from the lymphoid cells of said host;
   (iii) selecting said hybridoma to produce said monoclonal antibody; and
   (iv) obtaining said monoclonal antibody.

37. The method of claim 36, wherein said monoclonal antibody further has less than 20% cross reactivity with nitrotoluene.

38. The method of claim 36, wherein said immunogen has the formula

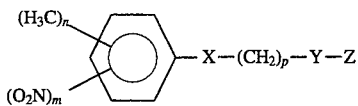

wherein

X and Y are each, independently

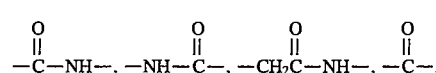

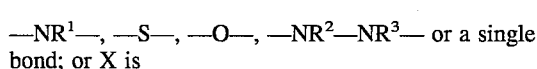

—NR$^1$—, —S—, —O—, —NR$^2$—NR$^3$— or a single bond; or X is

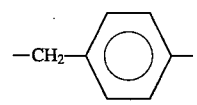

or —COO—; wherein R$^1$–R$^3$ are each, independently, selected from the group consisting of H, C$_1$–C$_2$ alkyls, and linear, branched and cyclic C$_3$–C$_6$ alkyls;

n is 0 or 1;

m is an integer from 1 to 3;

p is 0 or an integer from 1 to 4; and

Z is an immunologic carrier molecule.

39. The method of claim 38, wherein said immunogen carrier molecule Z is a compound selected from the group consisting of albumin, hemocyanin, thyroglobulin, polyamino acids and derivatives thereof.

* * * * *